United States Patent
Riondel et al.

(10) Patent No.: US 6,673,884 B2
(45) Date of Patent: Jan. 6, 2004

(54) METHOD FOR MAKING MONOMERS WITH TWO QUARTERNARY AMINO GROUP AND (CO)POLYMERS OBTAINED FROM SAID MONOMERS

(75) Inventors: Alain Riondel, Forbach (FR); Denis Tembou N'Zudie, Serquigny (FR); Marc Esch, Freyming Medebach (FR); Vladimir Chaplinski, Saint Avoid (FR); Didier Vanhoye, Breuil le Vert (FR)

(73) Assignee: Atofina, Puteaux (FR)

( * ) Notice: Subject to any disclaimer, the term of this patent is extended or adjusted under 35 U.S.C. 154(b) by 0 days.

(21) Appl. No.: 09/959,622

(22) PCT Filed: Jan. 19, 2001

(86) PCT No.: PCT/FR01/00182

§ 371 (c)(1),
(2), (4) Date: Aug. 28, 2002

(87) PCT Pub. No.: WO01/55089

PCT Pub. Date: Aug. 2, 2001

(65) Prior Publication Data

US 2003/0050417 A1 Mar. 13, 2003

(30) Foreign Application Priority Data

Jan. 24, 2000 (FR) .......................... 00 00834

(51) Int. Cl.[7] .................................. C08F 126/00
(52) U.S. Cl. ..................... 526/312; 560/222
(58) Field of Search ................. 526/312; 560/222

(56) References Cited

FOREIGN PATENT DOCUMENTS

| CZ | 250962 | | 3/1988 |
|----|--------|---|--------|
| FR | 1529000 | * | 5/1968 |

OTHER PUBLICATIONS

Solovskii, M. et al.: "Synthesis and antimcrobial properties of mono– and polymeric quaternary ammonium salts containing aminoalkyl esters of methacrylic acid" KHIM.– FARM. ZH. (1974), 8(6), 20–4, 1974, XP000952593 p. 348; tableau 1 p. 349.

* cited by examiner

Primary Examiner—Bernard Lipman
(74) Attorney, Agent, or Firm—Millen, White, Zelano & Branigan, P.C.

(57) ABSTRACT

To prepare compound (I), a quaternising agent $R^3-X^\ominus$ is introduced into a solution, in an organic solvent or a mixture of organic solvents, of a compound of formula (III), at a temperature of 35 to 80° C., and the reaction is then allowed to continue at said temperature until compound (III) has disappeared completely or substantially completely, after which water is added and then an aqueous solution of compound (I) is separated and the water removed as necessary.

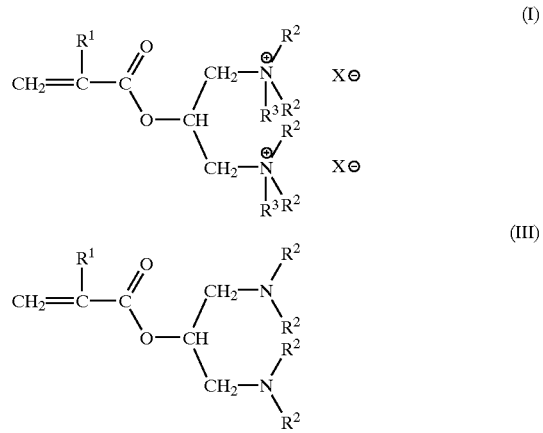

$R^1$=H or —$CH_3$; $R^2$=one of —$CH_3$, —$C_2H_5$, —$C_3H_7$ and —$C_4H_9$; the two $R^3$ are the same or different and each represents one of —$CH_3$, —$C_2H_5$, —$C_3H_7$, —$C_4H_9$ and —$CH_2C_6H_5$; and the two $X^\ominus$ are the same or different and each represents $Cl^\ominus$ or $Br^\ominus$.

21 Claims, No Drawings

METHOD FOR MAKING MONOMERS WITH TWO QUARTERNARY AMINO GROUP AND (CO)POLYMERS OBTAINED FROM SAID MONOMERS

The present invention relates to a method of manufacturing monomers with tertiary and/or quaternary amino groups.

Compounds of the type having formula:

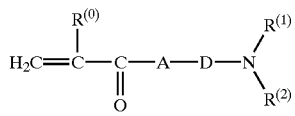

in which;

$R^{(0)}$ represents H or $CH_3$;

A represents —O— or —NH—;

D represents a $C_1$–$C_6$ linear or branched alkylene chain;

$R^{(1)}$ and $R^{(2)}$, the same or different, each represent independently H or at $C_{1-5}$-alkyl;

are well known from the background literature.

Important compounds in this family are N,N-dimethylamino ethyl acrylate (ADAME) and N,N-dimethylamino ethyl methacrylate (MADAME):

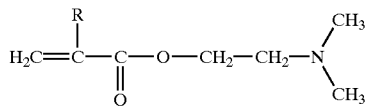

where R=H or $CH_3$.

A very large number of publications and patents describe the manufacture of aqueous solutions of quaternary ammonium salts ((M)ADAMQUAT) based on ADAME and MADAME respectively, the most representative of these salts being expressed by the formula:

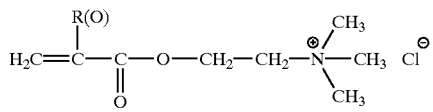

where R=H or —$CH_3$ and $R^{(3)}$=—$CH_3$ or benzyl ((M)ADAMQUAT MC or (M)ADAMQUAT BZ depending on whether $R^{(3)}$ represents $CH_3$ or benzyl).

This reaction is a quaternisation, in the presence of water, of the initial compound with a quaternising agent $R^{(3)}$—Cl.

The resultant aqueous solutions of quaternary salts are used in particular to prepare polymers intended for use as cationic flocculants in the treatment of water.

During research and development work on these polymers, the applicant company has discovered that compounds of formula (I):

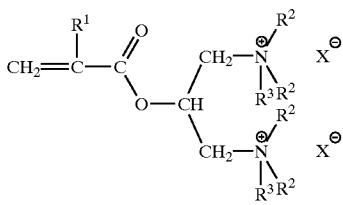

in which:

$R^1$ represents H or —$CH_3$;

$R^2$ represents one of —$CH_3$, —$C_2H_5$, —$C_3H_7$ and —$C_4H_9$;

the two $R^3$ are the same or different and each represents one of —$CH_3$, —$C_2H_5$, —$C_3H_7$, —$C_4H_9$ and —$CH_2C_6H_5$; and the two $X^\ominus$ are the same or different and each represents $Cl^\ominus$ or $Br^\ominus$, known by CZ-A-250 962, and in particular those in which $R^2$=$CH_3$, $R^3$=$CH_3$ or benzyl and where $X^\ominus$=$Cl^\ominus$ (which are denoted here by the abbreviation (M)ADAMQUAT 2MC or 2BZ depending on whether $R^3$ represents $CH_3$ or benzyl), enable aqueous dispersions to be prepared, either saline or without salt, thereby offering a solution to technical problems facing the person skilled in the art, these dispersions forming the subject matter of three French patent applications filed this day in the name of the applicant company.

Accordingly, the underlying objective of the present invention is to propose a method of manufacturing compounds having formula (I) as defined above, characterised in that at least one quaternising agent of formula (II):

in which $R^3$ and $X^\ominus$ are as defined above, is introduced into a solution, in an organic solvent or in a mixture of organic solvents, of a compound having formula (III):

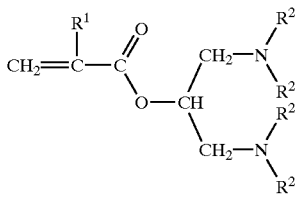

in which $R^1$ and $R^2$ are as defined above, at a temperature of 35 to 80° C., then the reaction is allowed to continue at said temperature, until compound (III) has disappeared completely or substantially completely, after which water is added and then an aqueous solution of compound (I) is separated and the water removed as necessary.

An example of a compound (I) is a compound having formula (Ia):

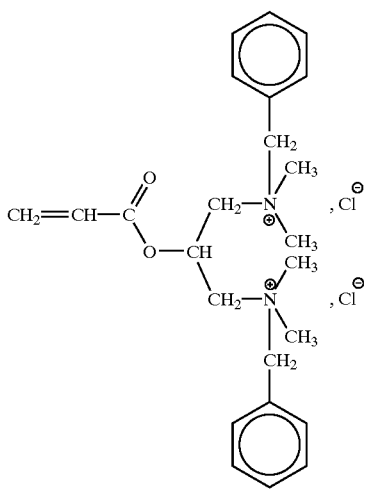

(Ia)

which may be designated by the abbreviation S-ADAMQUAT 2BZ.

Advantageously, the reaction is conducted with a molar ratio of quaternising agent (II)/compound (III) in a range of between 1.8 and 3.

The organic solvent used is chloroform, dichloromethane or dichloroethane, for example. A mixture of such solvents may also be used.

The reaction is not generally conducted under pressure unless the quaternising agent (II) is in the gaseous state.

The quaternising agent (II) is introduced into the solution of compound (III), generally over a period of 0.5 to 2 hours, and, once all the quaternising agent *has been introduced, the reaction of compounds (II) and (III) is conducted, generally over a period of 10 to 40 hours.

After separating the aqueous solution of compound (I), it is preferable to remove all traces of organic solvent from the resultant aqueous solution by stripping in air at a reduced pressure.

Said method results in an aqueous solution with a concentration of compound (I) which is preferably between 65 and 75% by weight.

According to one specific feature of the above method, it is conducted in the presence of at least one stabiliser selected in particular from hydroquinone, hydroquinone methyl ether and 3,5-ditert.-butyl-4-hydroxytoluene and mixtures of these stabilisers, the content of stabilising agent(s) being in particular 400 to 2000 ppm relative to the aqueous solution of the final compound (I).

Compound (III) may be prepared by causing a compound of formula (IV):

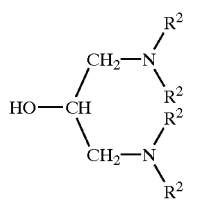

(IV)

in which $R^2$ is as defined above, to react with (meth)acrylic anhydride in the presence of triethylamine, with, a molar ratio of (meth)acrylic anhydride/compound (IV) of 0.5 to 2, at a temperature of 20 to 100° C., in particular 30 to 60° C., for a period of 2 to 10 hours in the presence of at least one stabiliser such as phenothiazine, hydroquinone methyl ether, 3,5-ditert.-butyl-4-hydroxytoluene and hydroquinone and mixtures of these stabilisers in a ratio of 200 to 3000 ppm relative to the charge.

In the reaction with (meth)acrylic anhydride, the triethylamine acts as a catalyst for the reaction, and traps the resultant (meth)acrylic acid in the salt form. It is generally used in an equivalent molar ratio of 1 to 2 relative to the (meth,)acrylic anhydride.

Another objective of the present invention is to propose homopolymers or copolymers containing units of at least one monomer of formula (I) obtained by the method as defined above.

The copolymers based on the monomers (I) incorporating the monomer (Ia) may be water-soluble or hydrophobic polymers in the form of an aqueous dispersion, latex, aqueous solution, inverse emulsion or powder. They are prepared by radical copolymerisation using various synthesis methods such as polymerisation in dispersion, solution, direct emulsion, inverse emulsion and inverse suspension.

The examples below, given by way of illustration only, provide a clearer understanding of the invention. In these examples, the specified proportions and percentages are by weight, unless stated to the contrary.

The following abbreviations are used in these examples:

S-ADAME: compound of formula:

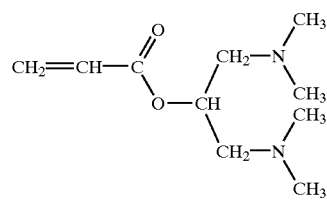

EMHQ: hydroquinone methyl ether.

EXAMPLE 1

Synthesis of S-ADAME

The following are introduced into a 1 litre glass reactor:

292 g of 1,3-bis-dimethylamino-2 propanol;

242 g of triethylamine; and 0.373 g of phenothiazine as a stabiliser.

226 g of acrylic anhydride are then added to this mixture over a period of 1 hour at ambient temperature, under agitation and bubbling in air. The temperature increases, reaching 50° C. After an additional 2 hours reaction time, the mixture is cooled and 50 ml of water are added. After decanting, 450 g of a higher organic phase are obtained, which is distilled under reduced pressure to separate 250 g of the above compound (purity GC≧99%).

EXAMPLE 2

Quaternisation of S-ADAME to Produce S-ADAMQUAT 2BZ

The S-ADAME obtained at point (a), stabilized with 1500 ppm of hydroquinone methyl ether and 150 g of $CHCl_3$, is introduced in a quantity of 44.2 g into a 250 ml glass reactor. Under agitation and whilst bubbling in air, the mixture is raised to 50° C. over a period of 1 hour, 55.9 g of benzyl chloride are added. After a reaction time of 25 hours, the initial acrylate has disappeared and 33 g of water are added. A higher phase is decanted and any traces of $CHCl_3$ removed by air stripping at 45° C. under reduced pressure (P=1.33× $10^4$ Pa (100 mm Hg)). 115.2 g of aqueous solution are thus obtained, containing 75% of quaternary cationic monomer of the anticipated structure, determined by RMN $^{13}C$. This monomer, is called S-ADAMQUAT 2BZ.

What is claimed is:

1. A method of manufacturing a compound having formula (I):

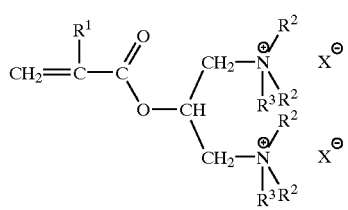

in which:

R$^1$ represents H or —CH$_3$;

R$^2$ represents one of —CH$_3$, —C$_2$H$_5$, —C$_3$H$_7$ and —C$_4$H$_9$;

the two R$^3$ are the same or different and each represents one of —CH$_3$, —C$_2$H$_5$, —C$_3$H$_7$, —C$_4$H$_9$ and —CH$_2$C$_6$H$_5$; and the two X$^\ominus$ are the same or different and each represents Cl$^\ominus$ or Br$^\ominus$, characterised in that at least one quaternising agent of formula (II):

 (II)

in which R$^3$ and X$^\ominus$ are as defined above, is introduced into a solution, in an organic solvent or in a mixture of organic solvents, of a compound having formula (III):

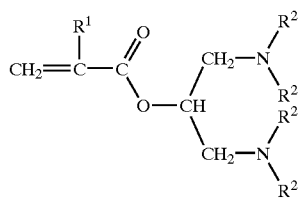

in which R$^1$ and R$^2$ are as defined above, at a temperature of 35 to 80° C., then the reaction is allowed to continue at said temperature until compound (III) has disappeared completely or substantially completely, after which water is added and then an aqueous solution of compound (I) is separated and the water removed as necessary.

2. A method as claimed in claim 1, wherein the reaction is conducted with a molar ratio of quaternising agent (II)/compound (III) in a range of between 1.8 and 3.

3. A method as claimed in claim 1, wherein the organic solvent used is at least one selected from the group consisting of chloroform, dichloromethane and dichloroethane.

4. A method as claimed in claim 1, wherein it is conducted under pressure if and wherein the quaternising agent (II) is in the gaseous state.

5. A method as claimed in claim 1, wherein the quaternising agent (II) is introduced into the solution of compound (III) over a period of 0.5–2 hours.

6. A method as claimed in claim 5, wherein once all of the quarternising agent has been introduced, the reaction between compounds (II) and (III) is conducted for a period of between 10 and 40 hours.

7. A method as claimed in claim 6, resulting in an aqueous solution with a concentration of 65 to 75% by weight of compound (I).

8. A method as claimed in claim 7, wherein all traces of organic solvent are removed from the resultant aqueous solution by stripping in air at a reduced pressure.

9. A method according to claim 8, wherein R$^3$ is benzyl.

10. A method according to claim 9, wherein R$^1$ is hydrogen.

11. A method as claimed in claim 1, wherein once all of the quaternising agent has been introduced, the reaction between compounds (II) and (III) is conducted for a period of between 10 and 40 hours.

12. A method as claimed in claim 1, wherein all traces of organic solvent are removed from the resultant aqueous solution by stripping in air at a reduced pressure.

13. A method as claimed in claim 1, resulting in an aqueous solution with a concentration of 65 to 75% by weight of compound (I).

14. A method as claimed in claim 1, wherein it is conducted in the presence of at least one stabiliser selected from the group consisting of hydroquinone, hydroquinone methyl ether and 3,5-ditert.-butyl-4-hydroxytoluene and mixtures of these stabilisers, the content of stabilising agent (s) being in particular from 400 to 2000 p.m. relative to the aqueous solution of the final compound (I).

15. A method as claimed in claim 1, wherein compound (III) is prepared by causing a compound of formula (IV).

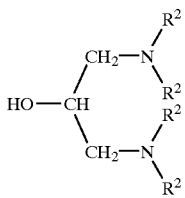

in which R2 is as defined above, to react with (meth)acrylic anhydride in the presence of triethylamine, with a molar ratio of (meth)acrylic anhydride/compound (IV) of 0.5 to 2, at a temperature of 20 to 100° C., for a period of 2 to 10 hours in the presence of at least one stabiliser selected from the group consisting of phenothiazine, hydroquinone methyl ether, 3,5-ditert.-butyl-4-hydroxytoluene and hydroquinone and mixtures of these stabilisers in a ratio of 200 to 3000 ppm relative to the charge.

16. A method according to claim 1, wherein R$^3$ is benzyl.

17. Homopolymers or copolymers containing units of at least one monomer of formula (I) obtained by the method as defined in claim 16.

18. A method according to claim 16, wherein R$^1$ is hydrogen.

19. A method as claimed in claim 18, resulting in an aqueous solution with a concentration of 65 to 75% by weight of compound (I).

20. Homopolymers or copolymers containing units of at least one monomer of formula (I) obtained by the method as defined in claim 18.

21. Homopolymers or copolymers containing units of at least one monomer of formula (I) obtained by the method as defined in claim 1.

* * * * *

UNITED STATES PATENT AND TRADEMARK OFFICE
CERTIFICATE OF CORRECTION

PATENT NO. : 6,673,884 B2
DATED : January 6, 2004
INVENTOR(S) : Alain Riondel et al.

It is certified that error appears in the above-identified patent and that said Letters Patent is hereby corrected as shown below:

Title page, Item [54] and Column 1, line 2,
reads "QUARTERNARY" should read -- QUATERNARY --
reads "AMINO GROUP" should read -- AMINO GROUPS --

Column 5,
Line 60, reads "dichioromethane" should read -- dichloromethane --
Line 63, reads "pressure if and" should read -- pressure and --

Column 6,
Line 28, reads "400 to 2000 p.m." should read -- 400 to 2000 ppm --
Line 42, reads "R2" should read -- $R_2$ --

Signed and Sealed this

Fifteenth Day of February, 2005

JON W. DUDAS
*Director of the United States Patent and Trademark Office*